(12) United States Patent
Andersen et al.

(10) Patent No.: US 8,578,932 B2
(45) Date of Patent: Nov. 12, 2013

(54) INHALER AND A METHOD OF OPERATING IT

(75) Inventors: Bjørn Knud Andersen, Struer (DK); Søren Christrup, Struer (DK); Jørgen Rasmussen, Struer (DK)

(73) Assignee: Bang & Olufsen Medicom A/S, Struer (DK)

( * ) Notice: Subject to any disclaimer, the term of this patent is extended or adjusted under 35 U.S.C. 154(b) by 238 days.

(21) Appl. No.: 12/737,362

(22) PCT Filed: Jun. 30, 2009

(86) PCT No.: PCT/EP2009/058167
§ 371 (c)(1),
(2), (4) Date: Jan. 20, 2011

(87) PCT Pub. No.: WO2010/003846
PCT Pub. Date: Jan. 14, 2010

(65) Prior Publication Data
US 2011/0114089 A1    May 19, 2011

Related U.S. Application Data

(60) Provisional application No. 61/129,659, filed on Jul. 10, 2008, provisional application No. 61/202,179, filed on Feb. 4, 2009.

(51) Int. Cl.
*A61M 16/00* (2006.01)
*A61M 11/00* (2006.01)

(52) U.S. Cl.
CPC .............. *A61M 16/00* (2013.01); *A61M 11/00* (2013.01)
USPC ............ 128/200.23; 128/200.14; 128/200.24; 128/203.12; 128/203.15

(58) Field of Classification Search
USPC ............. 128/200.11–200.24, 203.12, 203.15, 128/205.23
See application file for complete search history.

(56) References Cited

U.S. PATENT DOCUMENTS 3,826,413 A * 7/1974 Warren .................... 222/402.13
4,664,107 A    5/1987 Wass
5,027,808 A * 7/1991 Rich et al. ................ 128/203.23
5,217,004 A    6/1993 Blasnik et al.
(Continued)

FOREIGN PATENT DOCUMENTS

CA        2 640 679        2/2002
GB        2395909 A        6/2004
(Continued)

OTHER PUBLICATIONS

International Search Report.

*Primary Examiner* — Annette Dixon
(74) *Attorney, Agent, or Firm* — Harness, Dickey & Pierce, P.L.C.

(57) ABSTRACT

A Breath Actuated Inhaler having a canister with a medication dispensed when compressing the canister. Compression of the canister is prevented by a mechanism only allowing compression when an air flow is sufficient to ensure dispensing of the medication in the lungs/throat of the person. No latch or blocking mechanism is provided so that any force exerted by the person is, at all times, directed to the canister or preventing mechanism so that when no force is exerted by the user, no force is exerted in the inhaler. Prolonged exertion of such force could otherwise cause dimension changes and subsequent uncertainty of the dose size.

11 Claims, 21 Drawing Sheets

(56) References Cited

U.S. PATENT DOCUMENTS

| | | |
|---|---|---|
| 5,511,540 A | 4/1996 | Bryant et al. |
| 6,341,603 B1 | 1/2002 | Howlett |
| 8,225,790 B2 * | 7/2012 | Bowman et al. ......... 128/204.26 |
| 2002/0073992 A1 | 6/2002 | Andersson et al. |
| 2006/0289005 A1 | 12/2006 | Jones et al. |
| 2008/0156321 A1 | 7/2008 | Bowman et al. |

FOREIGN PATENT DOCUMENTS

| | | |
|---|---|---|
| GB | 2398252 A | 8/2004 |
| WO | WO 99/47199 | 9/1999 |
| WO | WO-2007141520 A1 | 12/2007 |
| WO | WO-2008142015 A2 | 11/2008 |

* cited by examiner

INHALER AND A METHOD OF OPERATING IT

CROSS-REFERENCE TO RELATED APPLICATIONS

This is a National Stage Application of International Application number PCT/EP2009/058167, filed on Jun. 30, 2009, and claims priority under 35 U.S.C. §119 to U.S. Provisional Application Nos. 61/129,659, filed on Jul. 10, 2008, and 61/202,179, filed on Feb. 4, 2009, the entire contents of each of which is herein incorporated by reference.

BACKGROUND a. Field

The present invention relates to improvements in inhalers and in particular to improvements in Breath Actuated Inhalers (BAIs).

b. Description of Related Art

A BAI is an inhaler type which does not dispense medication until the flow therein is sufficient. This flow is important to obtain the desired result of the medication.

In the situation where it is desired that the medication reaches the lungs, for example, the flow or flow rate and the droplet/powder size will determine whether the mediation impacts the throat of the person or whether it reaches the lungs. They will also determine whether medication having reached the lungs will impact the lungs and stay there or be exhaled again.

The droplet/powder size normally is controlled by the medication/valve/canister/nozzle and may normally not be altered by the user. The flow, however, is just as important, which is the reason for the use of BAIs.

Standard BAIs have a lockable spring which is loaded by the user and which is used for compressing the canister at a later point in time, where after the user needs not provide additional force and may concentrate only on inhaling sufficiently in order to receive the medication.

However such loaded springs may be loaded over extended periods of time, whereby the material receiving and restraining the force/load may experience material creep or deformation, which will lead to dimension changes to the dispenser. Such dimension changes may result in an insufficient compression of the canister or other disadvantages in the medication providing.

Another problem may be seen when compressing a canister for a prolonged period of time. Canisters are not guaranteed tight when compressed, so a leakage of medication or propellant may be experienced, which is a major problem due to the amount of medication and the number of doses no longer being exact.

In addition, as an inhalation normally is performed while maintaining the most commonly used canister in a vertical direction with the stem pointing downwardly, and as this direction is the optimal direction with respect to the dosing of the next dose, it is desired that the canister is actually also released or de-compressed in this direction.

SUMMARY

The present invention relates to solutions to these problems.

In a first aspect, the invention relates to a dispenser for providing aerosolized medication to a person, the dispenser comprising: a canister for outputting the medication upon compression of the canister along a predetermined direction with a predetermined force, the medication being output into a flow channel, means for preventing compression of the canister until a predetermined minimum flow is present in the flow channel, transferring means adapted to receive force from the user and to, at all times and in real time, transfer at least part of the force applied to the canister and/or the preventing means along the predetermined direction.

In this connection, a jet of aerosolized medication is a flow of medication entrained in air or gas as a powder, droplets or the like. Normally, the medication is stored in a container or canister together with a propellant which, when released to ambient pressure, expands and makes the medication disperse into the gas flow as fine droplets or powder, often with the aid of a nozzle of the dispenser.

Often, this jet or flow of mediation is inhaled by a person either through the nose or the mouth. Many requirements and wishes exist as to the powder/droplet size of the medication in order for it to reach the lungs or throat of the person, depending on the function of the medication, without being exhaled again. Naturally, the preventing means may be adapted to any inhalation flow (rate) desired.

A common type of canister is one which outputs the medication upon compression of the canister along a predetermined direction with a predetermined force. Normally, the canister will have an output stem which is displaceable in a direction into the canister and through which the medication is output during such displacement.

The dispenser has a flow path into which the medication is output from the canister and which the user may inhale. Normally, the medication is output from the canister via a nozzle positioned in the flow path. The flow of the flow path normally being created by the user due to the inhalation. This flow path normally is defined by parts of the inhaler, such as a housing thereof, but may also at least partly be open to the surroundings in order to enable the flow to take place.

A number of manners and means exist in the prior art of preventing compression of the canister, and all such manners and means may in principle be used, as long as these are operatable by or in response to the (inhalation) flow present in the flow channel. Thus, when the flow in the flow channel equals or exceeds the predetermined flow, the preventing means should allow compression of the canister.

Some manners or embodiments operate by preventing the force from reaching the canister and others act to prevent the canister from compressing even though the force is applied thereto. This is described in further detail further below.

In the present context, "in real time" means that no energy storing means, such as a lockable spring or latch, are used. "at all times" also means that no energy storing means or locking means are provided which may store energy or prevent a force from being applied or removed, at least when this force exceeds the force required to output a dose of the medication. Then any force variations provided by the user will be transferred, at least partly, to the canister/preventing means. Thus, if the user, having provided a force sufficient to compress the canister, decides that no inhalation is desired or required, the user may release the dispenser where after at least substantially no force is then provided to the canister/preventing means along the direction.

In one embodiment, the dispenser further has means for indicating to the user when the transferred force is equal to or exceeds the predetermined force. This has the advantage that medication will always be dispensed when the correct flow is provided, and that the user needs not provide excessive force in order to ensure that the force requirement is met.

This indication may be obtained in a number of manners. If the transferring means comprises a button or other element engaged by the user as well as a resilient element (see further below) by moving it in relation to a housing of the dispenser, an indication may be provided on the button in order for the user to see when a sufficient movement of the button has been reached and thus when a sufficient force is applied. This indication could be visible outside the housing or from inside the housing, such as via a window or opening therein.

Also, an indication could be tactile such as the providing of a stop of a movement (such as of the button or other movable element engageable by the user and providing the force), or a higher/lower friction part of the movement, or a part of the movement provided with e.g. a sound/vibration generating element or the like.

In a particular embodiment, the dispenser comprises a flow channel, wherein the indicating means comprises an element being adapted to at least substantially block the flow channel, when the transferred force is lower than the predetermined force but not when the force is equal to or exceeds the predetermined force. Thus, the person inhaling will be able to tell, whether the flow channel is obstructed or at least substantially obstructed, or whether a more free flow is possible. This will also give the user an indication of whether a sufficient force is provided.

It should be noted that the element obstructing the flow channel may form part of the preventing means in that this element will change, if the force provided is sufficient and when the flow is sufficient. Thus, if e.g. this element is a displaceable/rotatable flap element obstructing the flow channel, a sufficient force may allow rotation/displacement thereof by a sufficient inhalation flow. This rotation/displacement may then allow the canister to compress, in that the force applied and the flow provided are now sufficient.

In one preferred embodiment, the canister comprises an output element, the canister being compressible by displacing the output element in a direction toward other elements of the canister, such as a main medication container thereof, wherein the transferring means is adapted to transfer the force to the canister, and wherein the preventing means are adapted to prevent displacement of the output means in the direction toward the other elements of the canister.

The transferring means are adapted to receive force from the user and to transfer at least part of the force applied to the canister and/or preventing means along the predetermined direction. In this embodiment, the transferring means may simply be the end of the canister opposite to the output element, whereby the user engages the canister directly. In other situations, a button or other engageable element may be desired, optionally in combination with a resilient element, such as a spring, a foam, a gel, or the like, which the user may compress while providing the force thereto and to the canister. The advantage of the resilient element is that the user has a tactile sensation of providing the force, and the user may get (see above) an indication of the force actually provided.

In one situation, the output element may be stationary in relation to a housing of the dispenser, and the preventing means may be adapted to prevent the other parts (typically the main container/housing of the canister) from moving along the direction and toward the output element. Alternatively, the preventing means may allow, when any flow is not sufficient, movement of the output element in relation to the housing in that direction, so that the whole canister moves due to the force but with no compression. Then, compression may be facilitated by the preventing means fixing the output element in relation to the housing when the flow is sufficient.

In another preferred embodiment, the transferring means is adapted to transfer the force to the preventing means. In this situation, force along the direction (or at least force comparable to the predetermined force) is only transferred to the canister when the preventing means allow it.

In another embodiment, the transferring means is adapted to always, when not engaged by the user, transfer at least substantially no force to the canister/preventing means. This has the advantage that no force is applied which would bring about the danger of material creep or deformation which could render the operation of the dispenser less reliable.

In one embodiment, the dispenser further comprises means for preventing the canister from, upon compression, extending, until a force transferred by the transferring means is below a predetermined force. When this predetermined force is equal to or lower than that exerted by the canister upon compression, it is ensured, that the canister is allowed to fully extend. Normally, the metering of the next dose takes place during extension of the canister, whereby it is desired that the canister can fully extend and thus correctly meter the next dose.

In that or another embodiment, the transferring means comprise an element blocking the flow channel in a first position and opening the flow channel in another position. In this situation, the blocking takes place when a force below a predetermined force is received from the user, and the opening takes place when a force exceeding the predetermined force is received from the user. Thus, the transferring means will block the flow channel until the force received exceeds the predetermined force and will so again, if the force falls below the predetermined force.

Thus, it ensured that a flow cannot flow in the flow channel, until the force received is sufficient for compressing the canister and dispense the medication correctly.

Another aspect of the invention relates to a method of operating a dispenser according to the first aspect of the invention, the method comprising the steps of: the user providing a first force to the transferring means which transfer to the canister/preventing means a force exceeding the predetermined force, while any gas flow in the flow channel is lower than the predetermined flow, the user subsequently releasing the transferring means, whereby at least substantially no force is subsequently transferred to the canister/preventing means.

Consequently, even though sufficient force has been provided, where standard BAIs would then lock the biasing element (typically a spring), releasing the dispenser will, according to this aspect of the invention, release the force such that no locked biasing element is present.

Naturally, the method may also comprise the steps of providing the first force while inhaling, whereby the preventing means will allow compression of the canister and the release of medication.

BRIEF DESCRIPTION OF THE DRAWINGS

In the following, preferred embodiments of the application will be described with reference to the drawing, wherein.

DETAILED DESCRIPTION

Figure 1:
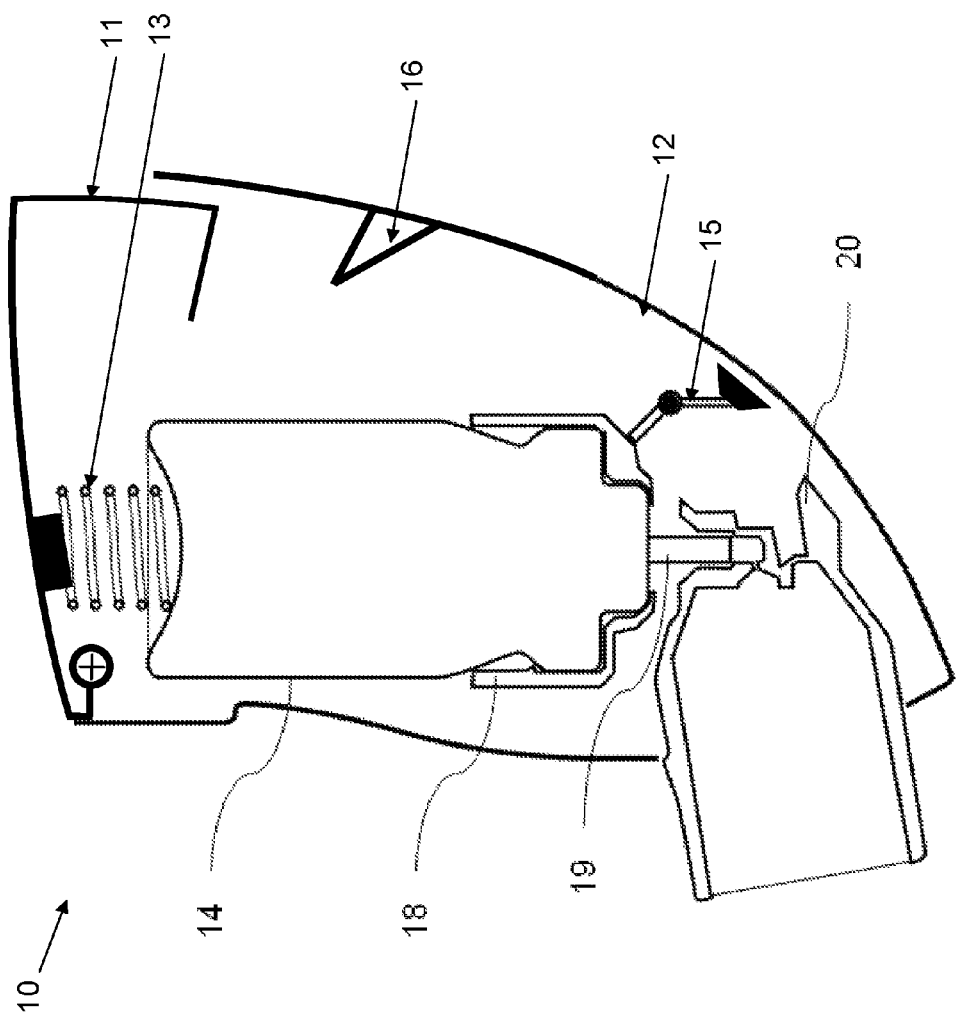
FIGS. 1-3 illustrate a first embodiment according to the invention.

In FIG. 1 illustrates an inhaler 10 in an unbiased state. The inhaler 10 has a housing 12 having therein a canister 14 holding the medication to be dispensed.

The canister 14 has a stem 19 through which the medication is output when the stem 19 is forced partly into the main part of the canister 14. When the canister 14 is compressed, the medication is output from the stem 19 and via a nozzle present in a mouth piece 20 into which the stem 19 extends and through which the person inhales the medication output. The stem 19 is fixed in the mouth piece 20, and the mouth piece 20 is fixed in relation to the housing 12.

The inhaler 10 further comprises a button 11 which is engageable by the user in a downward direction (in the drawing). Forcing the button 11 downwards will bias (see FIG. 2) a spring 13 positioned between the button 11 and the bottom of the canister 14.

Figure 2:
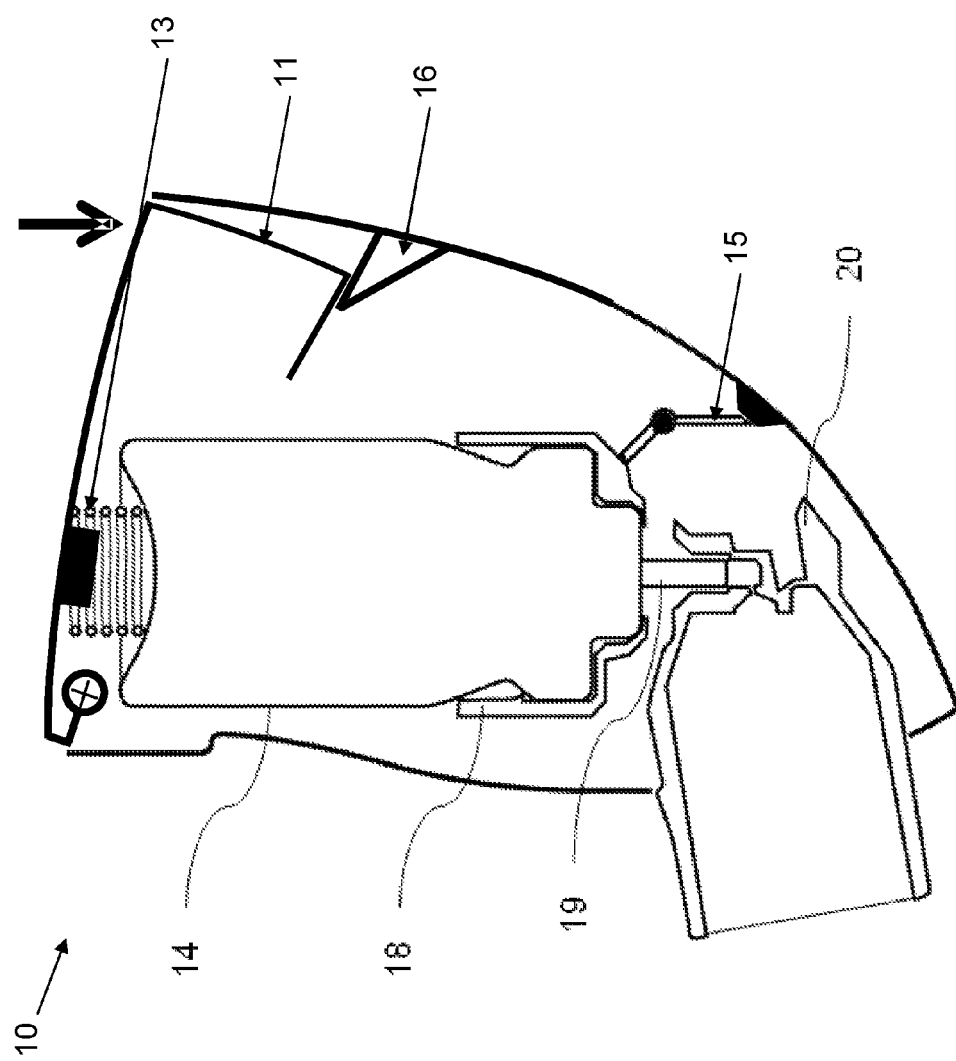

In the position illustrated in FIG. 2, the button is depressed to engage a stopping element 16 fixed to the housing 12. In this situation, the force provided by the user on the button 11 is sufficient for the force exerted by the spring 13 to be able to compress the canister 14.

However, an element 18 engaging a neck portion of the canister 14, prevents movement of the main part of the canister 14 downwards and thereby prevents compression of the canister 14 and dispensing of medication. The element 18, thus, is movable in the downward direction in relation to the housing 12 but is prevented from doing so by a flap element 15.

Figure 3:
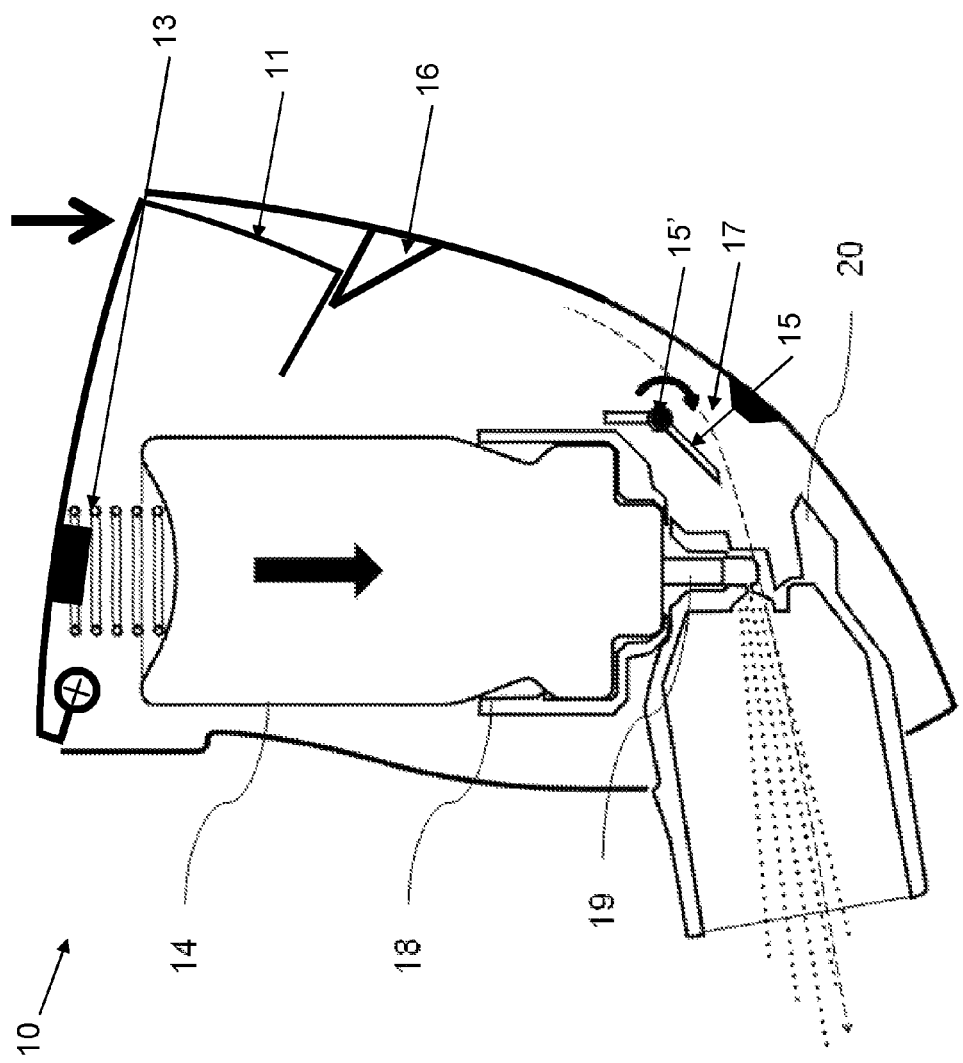

The operation of the flap element 15 may be seen by comparing FIGS. 2 and 3. The flap element 15 is rotatable around an axis 15'. In the locked position of FIG. 2, counter clockwise rotation is impossible due to the engagement of one end of the flap element 15 with the housing 12. As the other end engages the element 18, the element 18 is prevented from being moved downwards by the force exerted by the spring 13.

However, when the user inhales via the mouth piece 20, an air flow is created forcing the longest part of the flap element 15 clockwise, where after the element 18 is allowed to move downwards due to the force exerted by the spring 13, whereby mediation is dispensed into the mouth piece 20 and is inhaled by the user.

Naturally, the dimensions of the flap element 15 as well as those of the flow channel 17 in which the element 15 is positioned may be adapted to any particular situation, such as the determination of the flow required to release the element 18, the forces which must be handled due to the forces exerted by the spring 13, etc.

Figure 4:
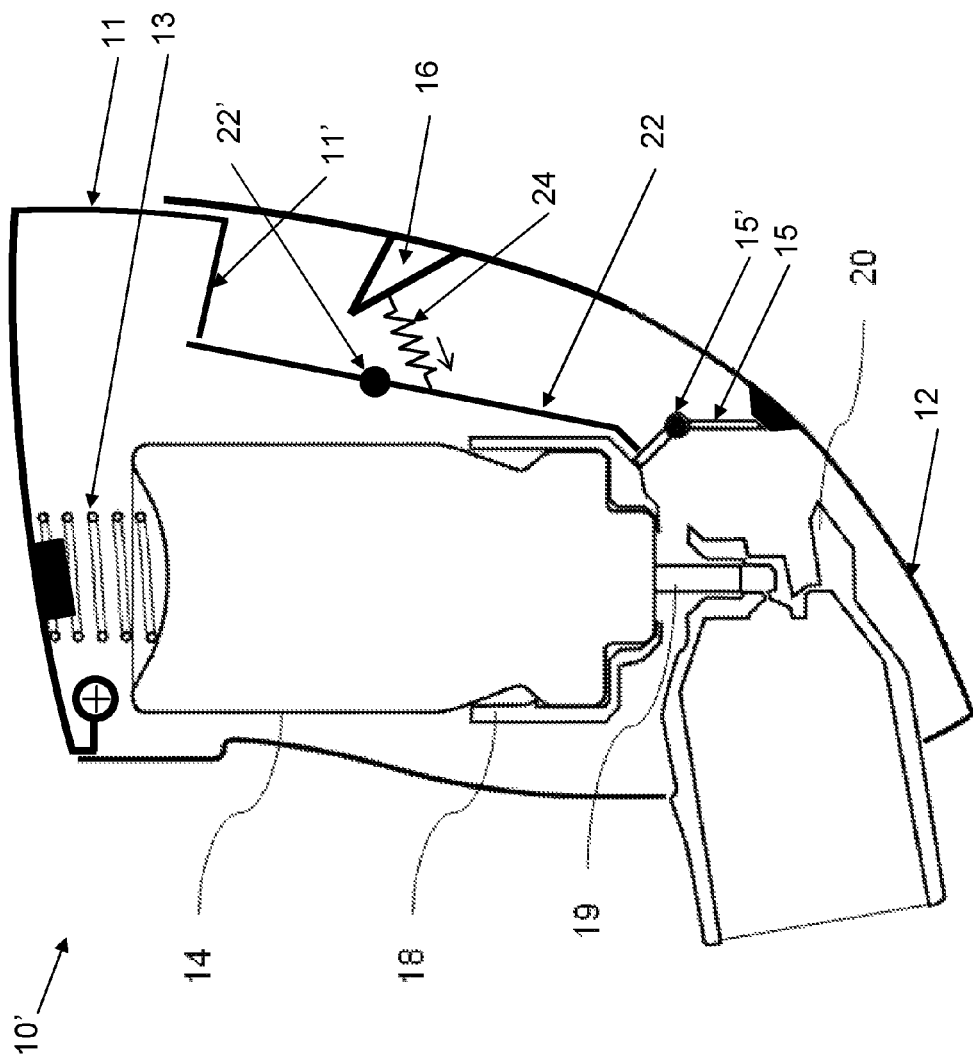
FIGS. 4-6 illustrate a second embodiment according to the invention.
Figure 5:
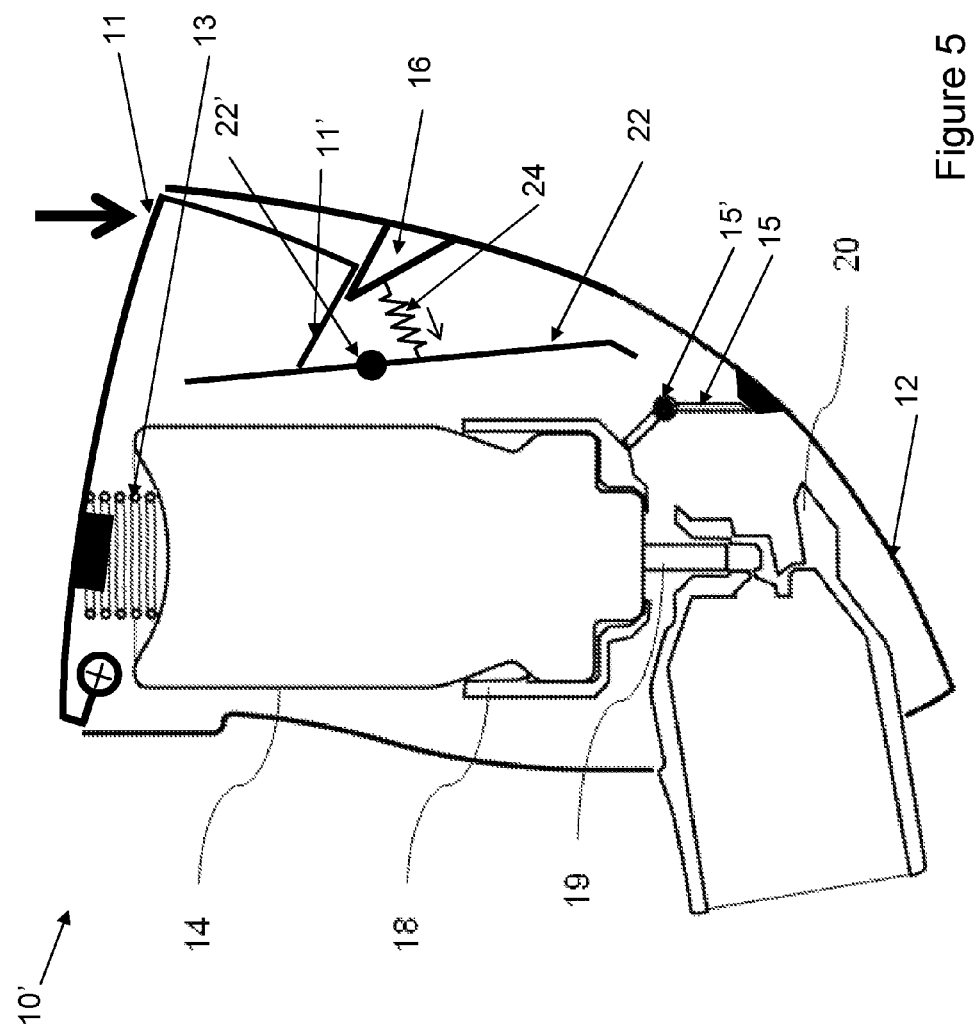
Figure 6:
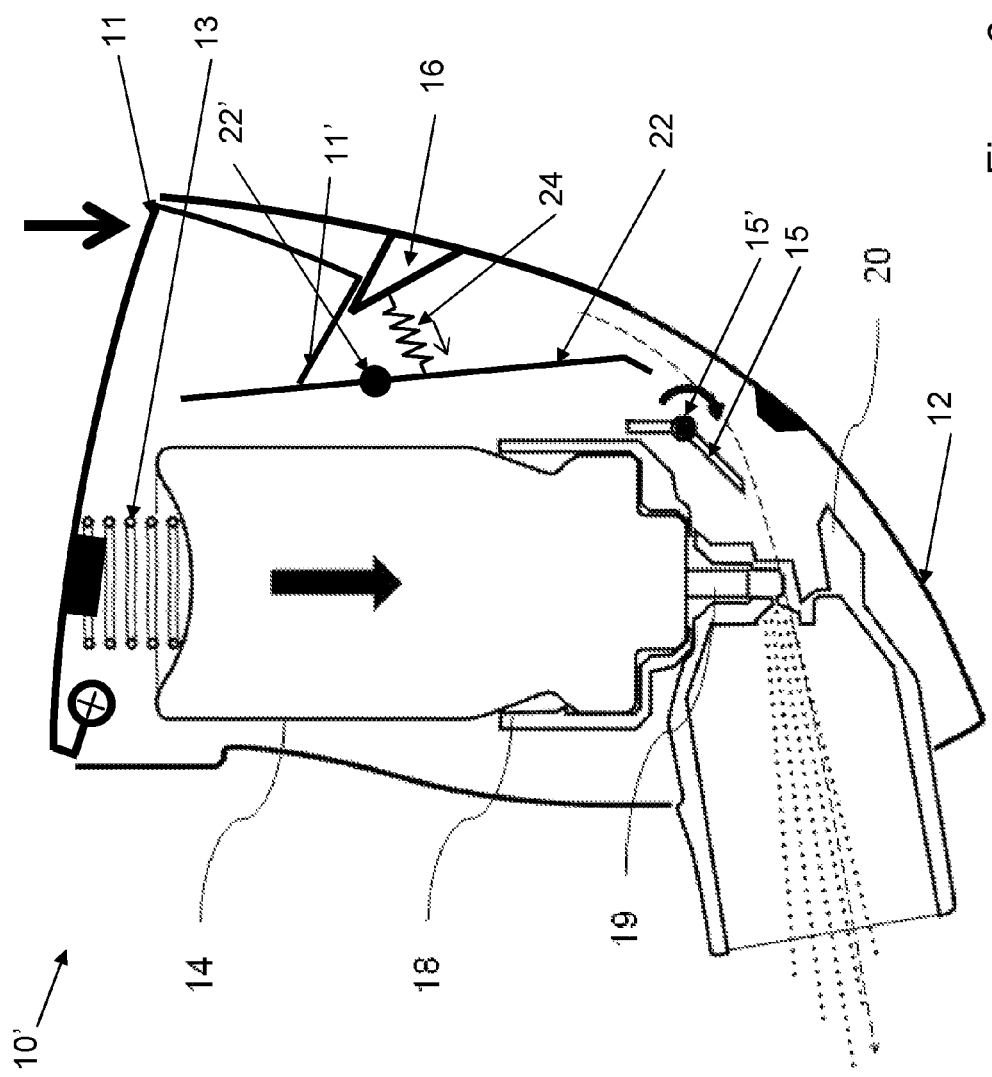

In FIGS. 4-6, an embodiment of an inhaler 10', having the same elements as that of FIGS. 1-3, is illustrated which further has a blocking element 22 which is rotatable around an axis 22' and which engages an inwardly directed part 11' of the button 11, when this is rotated/depressed.

The blocking element 22 acts, when the button 11 is not depressed, to prevent the flap element 15 from rotating clockwise, even if a sufficiently large flow was present, when the force exerted on the button 11 and thus on the canister 14 is not sufficient to ensure a suitable compression and thus dispensing of medication.

When the button 11, however, is depressed, the part 11' will act to rotate the blocking element 22 counter clockwise (see FIG. 5) so that the flap element 15 may act on a flow in the flow channel and mediation may be dispensed (see FIG. 6), if a sufficiently large flow is present.

Releasing the button 11 (having dispensed medication or not) will allow the blocking element 22 to rotate clockwise due to a spring 24 acting between the element 22 and the stopping element 16 (or alternatively another part of the housing 12).

Naturally, the blocking element 22 may be shaped in other manners and engage the button 11 (or other engaging element), as its primary function is to allow depression of the canister only in the situation where a sufficient force is exerted in order to ensure the desired compression of the canister and thus dispensing of medication.

In addition to the blocking means of FIGS. 4-6 or as an alternative thereto, other manners may be used for indicating to the user that the force exerted is sufficient or desired.

One manner may be seen in any of FIGS. 1-6 in that the stopping means 16 will indicate, when the button 11 engages the stopping means 16, that the force is sufficient.

Figure 7:
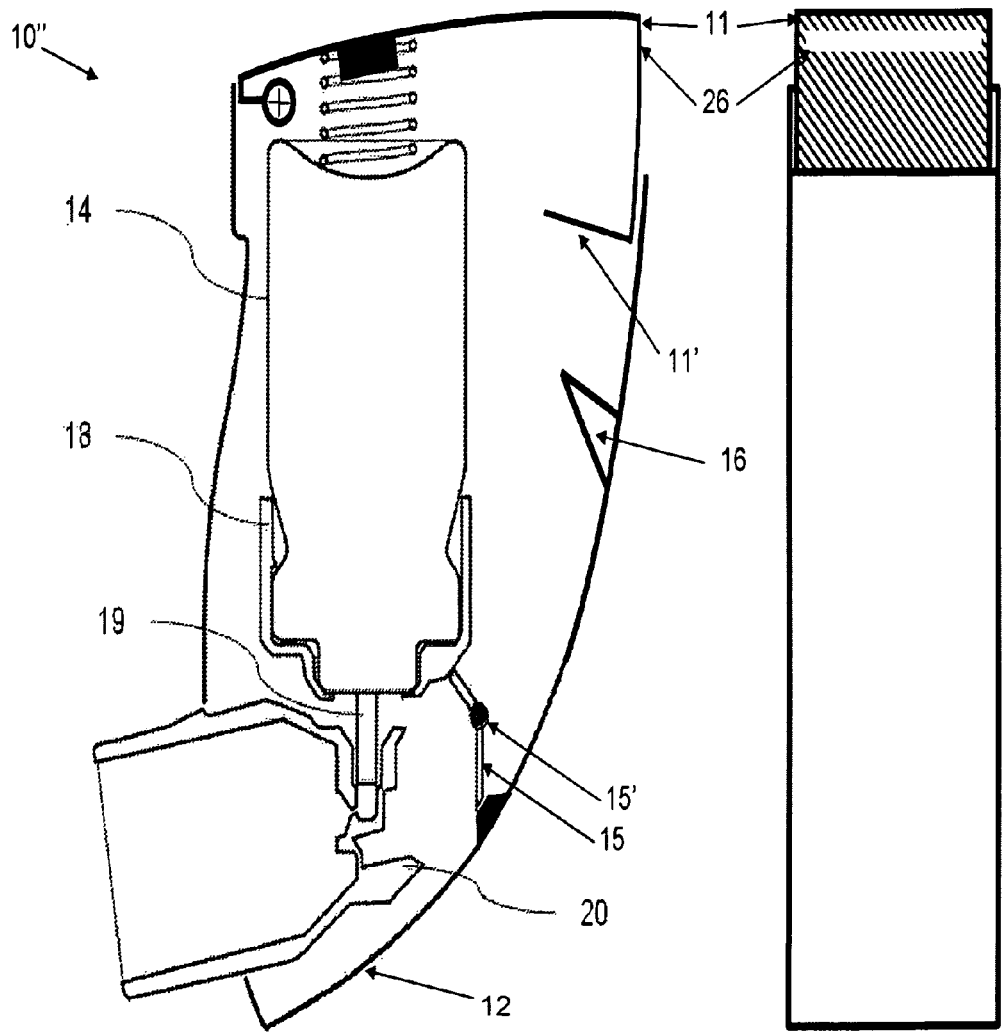
FIGS. 7 and 8 illustrate an embodiment indicating to the user when a sufficient force is exerted.
Figure 8:
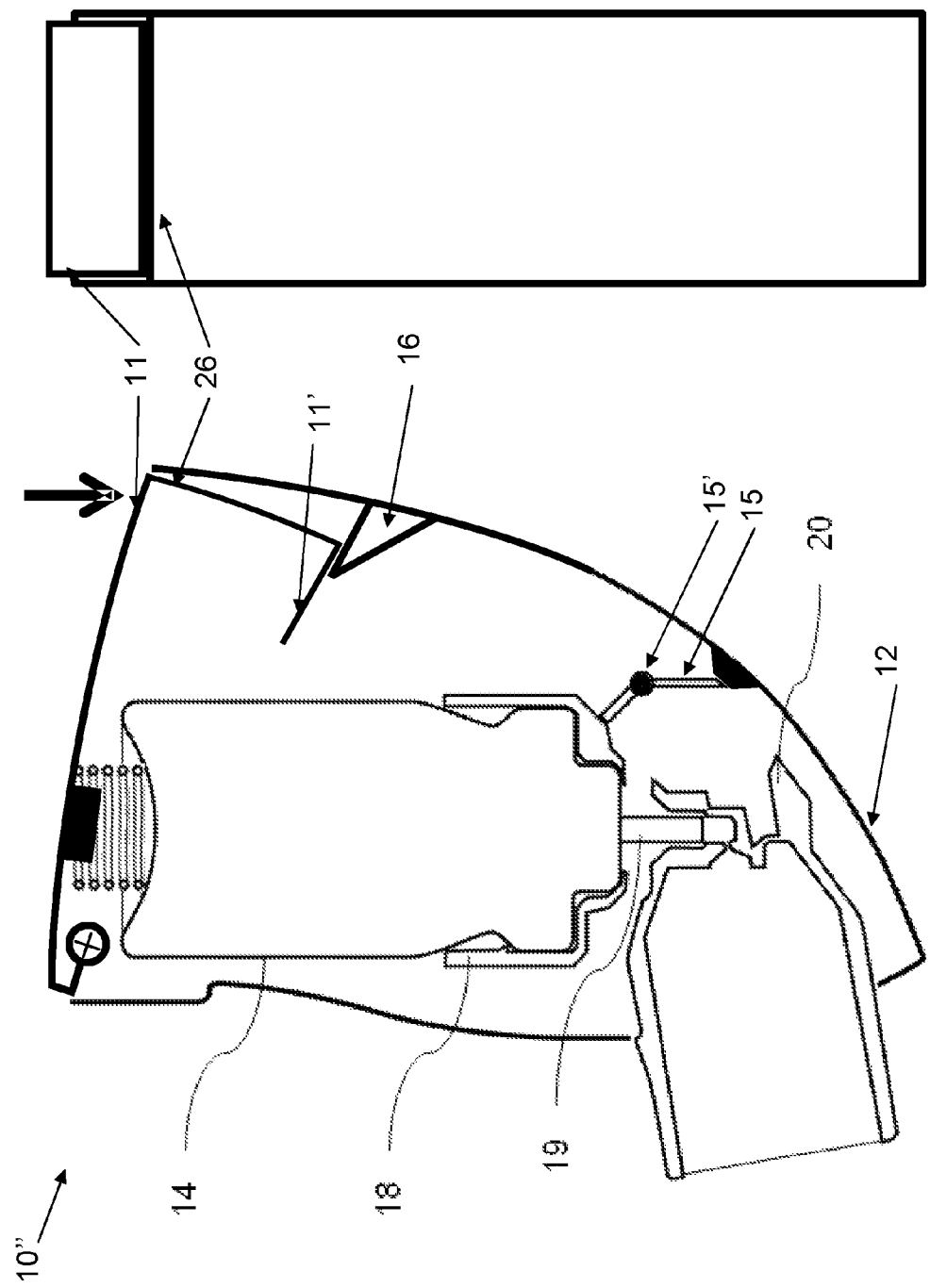

Other manners may be seen from FIGS. 7 and 8 illustrating an inhaler 10" having generally the same elements and operations of the inhalers 10 and 10', but wherein the button 11 has an indication 26 which is present when the button 11 is not depressed or is not sufficiently depressed, but which is hidden in the housing 12, when the button is sufficiently depressed, such as when the button 11 engages the stopping element 16, if present.

Other visualization means may be part of the button 11 visible in a transparent window (not illustrated) positioned at the top of the inhaler 10, through which different parts of the button 11 may be seen when the button 11 is sufficiently depressed and not sufficiently depressed, respectively. Naturally, one of the positions may not reveal a part of the button 11.

A particular manner of providing an indication to the user may be seen in combination with the embodiment 10' of FIGS. 4-6 wherein the flap element 15 is prevented from rotating, when the force is insufficient.

In this particular manner, the flap element 15 may block the flow path 17 to a degree where the user will be able to tell, from the flow resistance of the flap element 15 in the flow path and during inhalation, that the flap element 15 blocks or substantially blocks the flow path 17. When the force is sufficient, the flap element 15 is allowed to rotate, which then gives a noticeable change in flow resistance during inhalation.

Due to the operation being that the person must exert the force on the button 11 while performing the inhalation, it may be desired to not strain weaker persons too much so as to also have the strength and concentration to perform a correct inhalation. This may be obtained by ensuring that the force required during inhalation is not too high.

Figure 9:
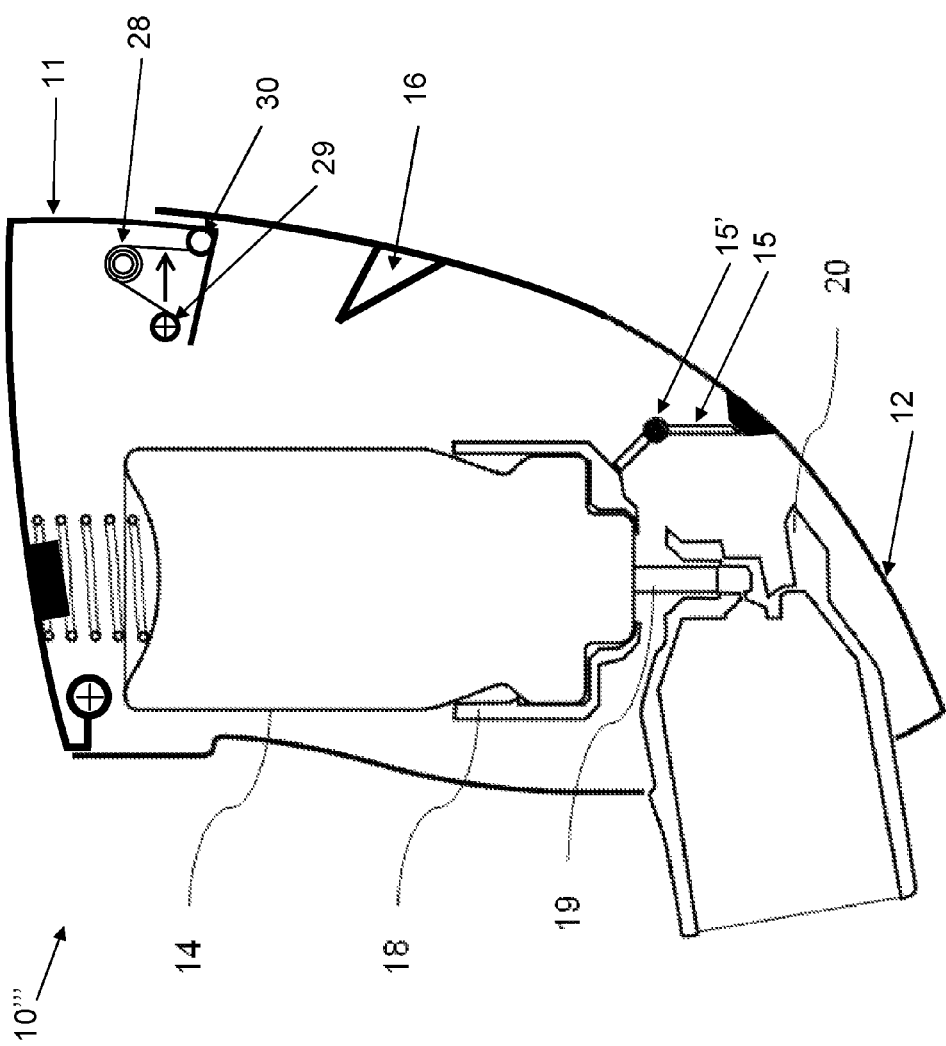
FIGS. 9-11 illustrate an embodiment having a non-linear actuation force.
Figure 10:
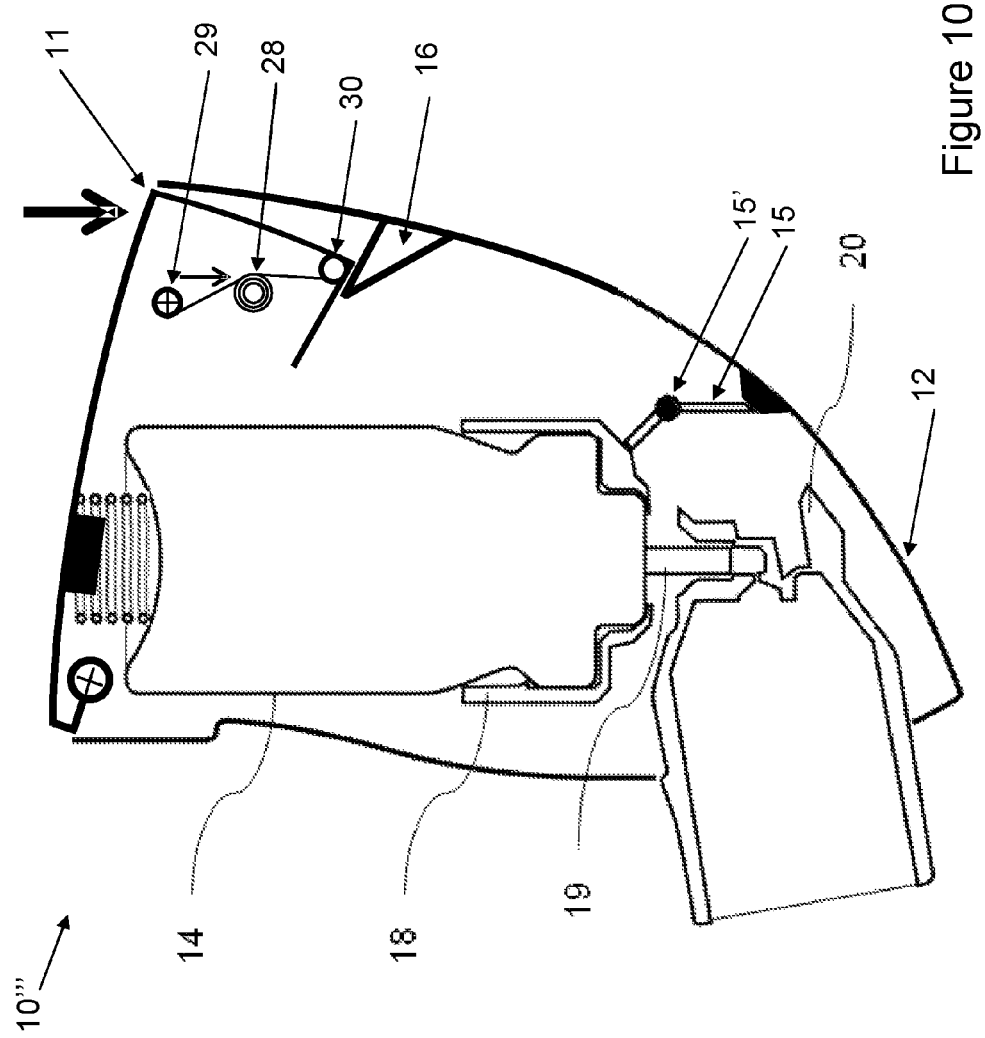
Figure 11:
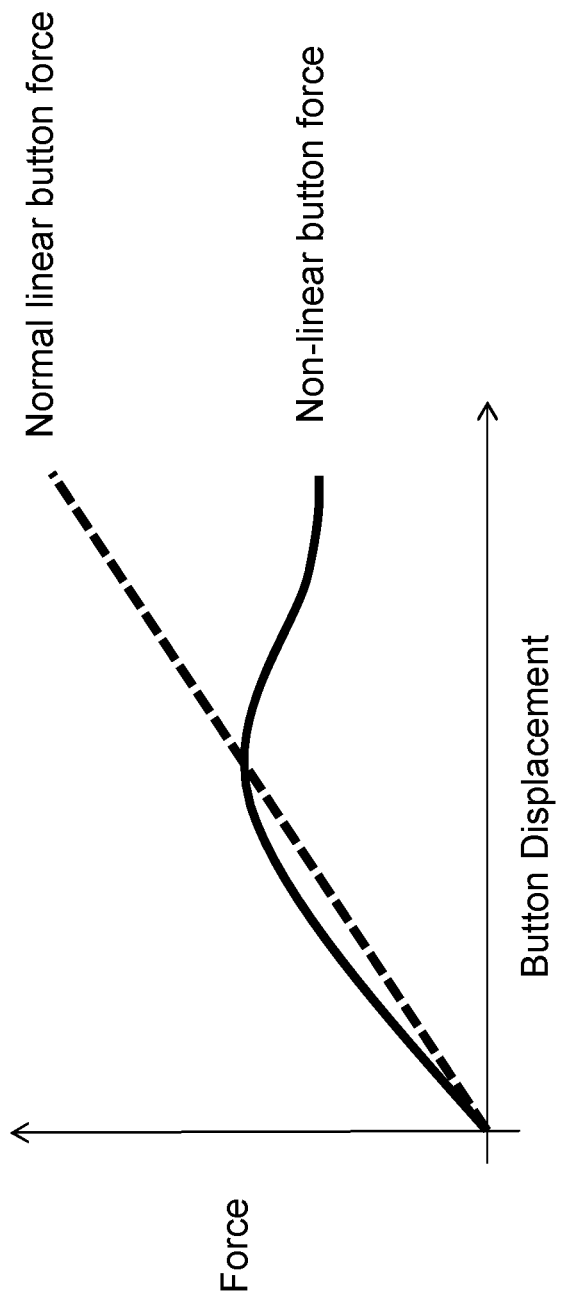

FIGS. 9-11 illustrate a way of providing a non-linear actuation force during depression of the button 11. In these figures, an embodiment is illustrated of an inhaler 10', having generally the same elements an operations as that of any of the above figures, further having a torsion spring 28 acting between the housing 12 and the button 11. The torsion spring 28 is adapted to bring its two engagement points or ends 29 and 30 as far away from each other as possible.

When the button 11 is not depressed (FIG. 9), the ends 29 and 30 are close to each other, and the force of the spring 28 acts generally in the horizontal plane—i.e. more or less perpendicular to the longitudinal direction of the canister. The spring constant experienced by the user when depressing the button 11 will be that of the spring 13.

Depressing the button 11 (FIG. 10) will bring a line intersecting the points 29 and 30 more along the direction of the canister 14, whereby the spring 28 will act to aid the compression of the spring 13. The spring constant experienced by the user will be that of the spring 13 less that of the spring 28.

Thus, the force required may be seen from FIG. 11, from which it is seen that the force will be slightly higher in the first part of the depression movement of the button 11, compared to the situation where the spring 28 is not used, but will be lower in the last part of the movement.

Thus, when the user has depressed the button 11, it will require less force to keep the button 11 depressed, whereby the user may be more easily capable of concentrating on the inhalation.

Figure 12:
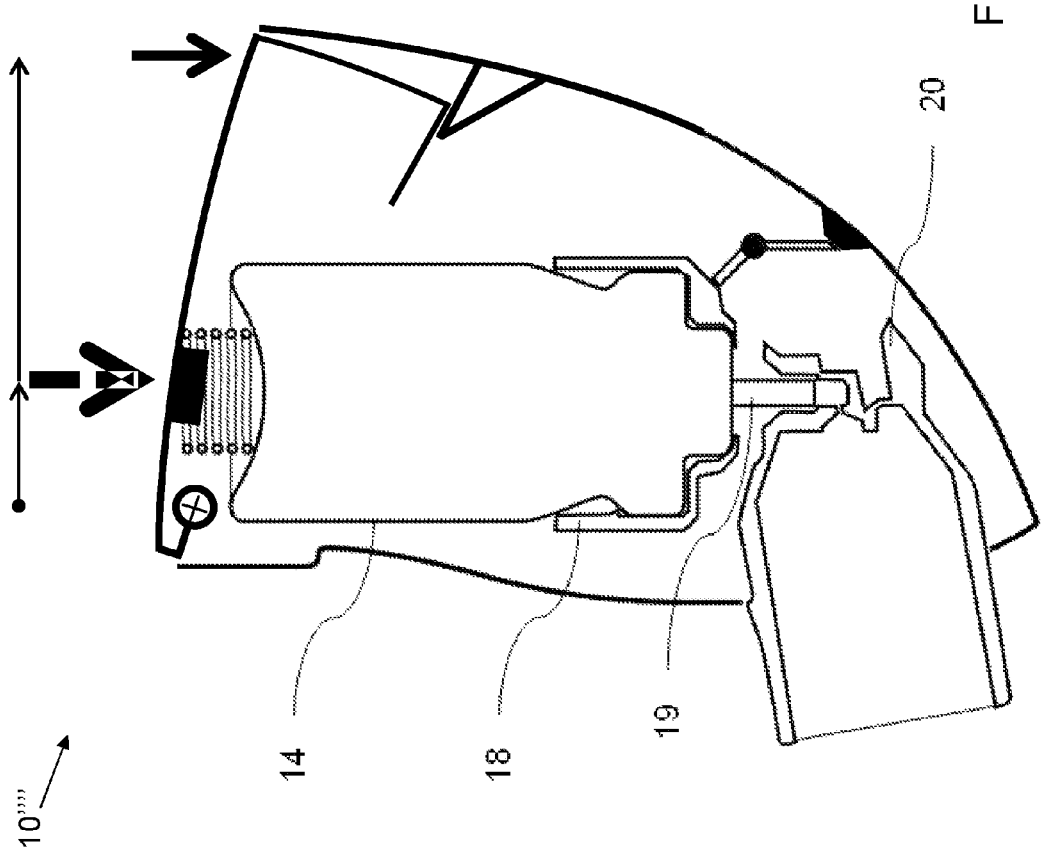
FIG. 12 illustrates an embodiment having a geared, linear actuation force.

FIG. 12 illustrates an embodiment 10''', again having generally the same operation and elements as the other figures, which has a gearing of the actuation force in order to also make depression easier for the user.

This gearing is simply provided by having the button 11 act as a lever, where the engagement point of the user (the rightmost arrow) is farther from the axis of rotation of the button 11 than the engagement point of the spring 13 (the leftmost arrow).

Thus, the actuation force is linear, but the force is lower in that the displacement required is larger—due to the operation of the lever.

Figure 13:
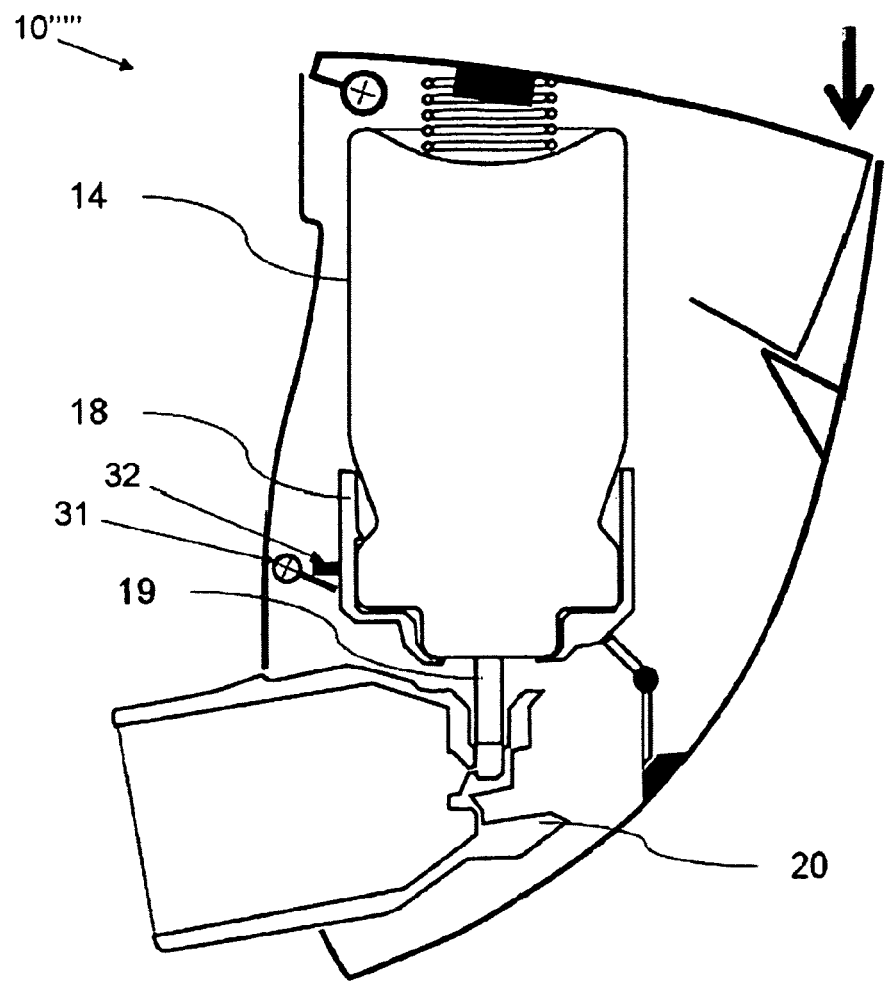
FIGS. 13 and 14 illustrate an embodiment comprising a dose counter.
Figure 14:
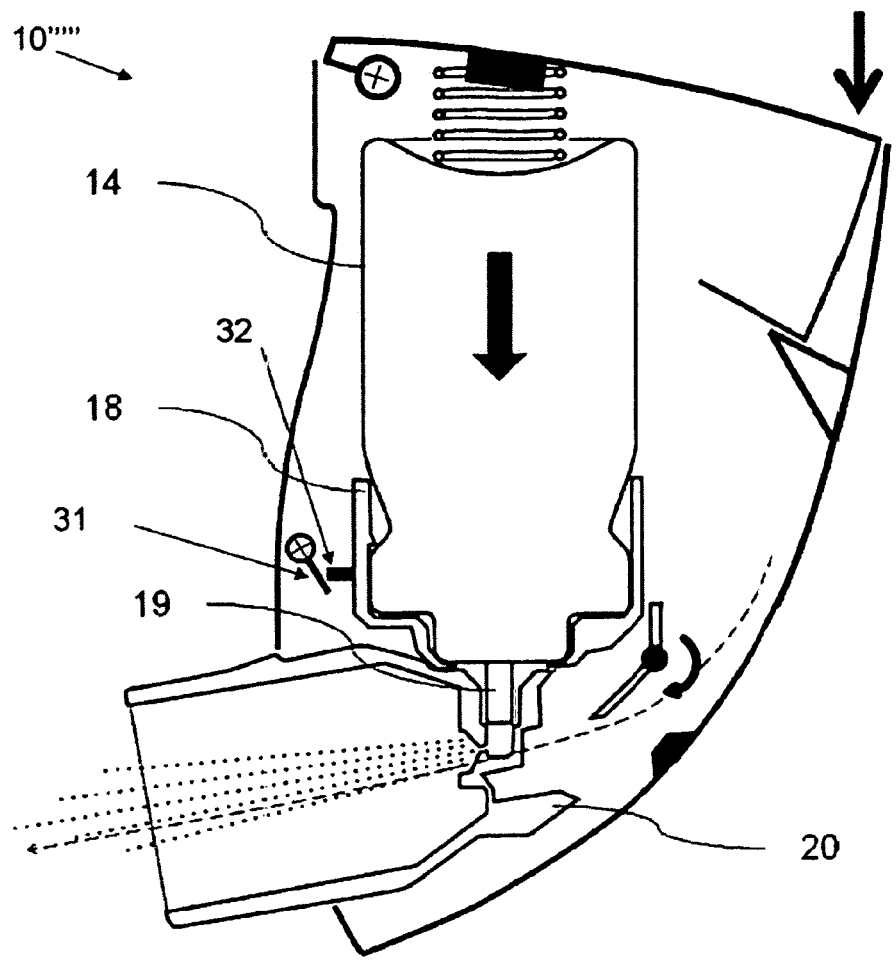

FIGS. 13 and 14 illustrate an embodiment 10'''', again having generally the same elements and operation as those of the other figures, further comprising a dose counter 31 having a rotatable or displaceable part engaging a part 32 of the element 18. The dose counter 31 is fixed in relation to the housing 12, whereby each compression of the canister 14, i.e. each dispensing of a dose of medication, is counted due to the relative displacement of the part 32 in relation to the dose counter 31.

Figure 15:
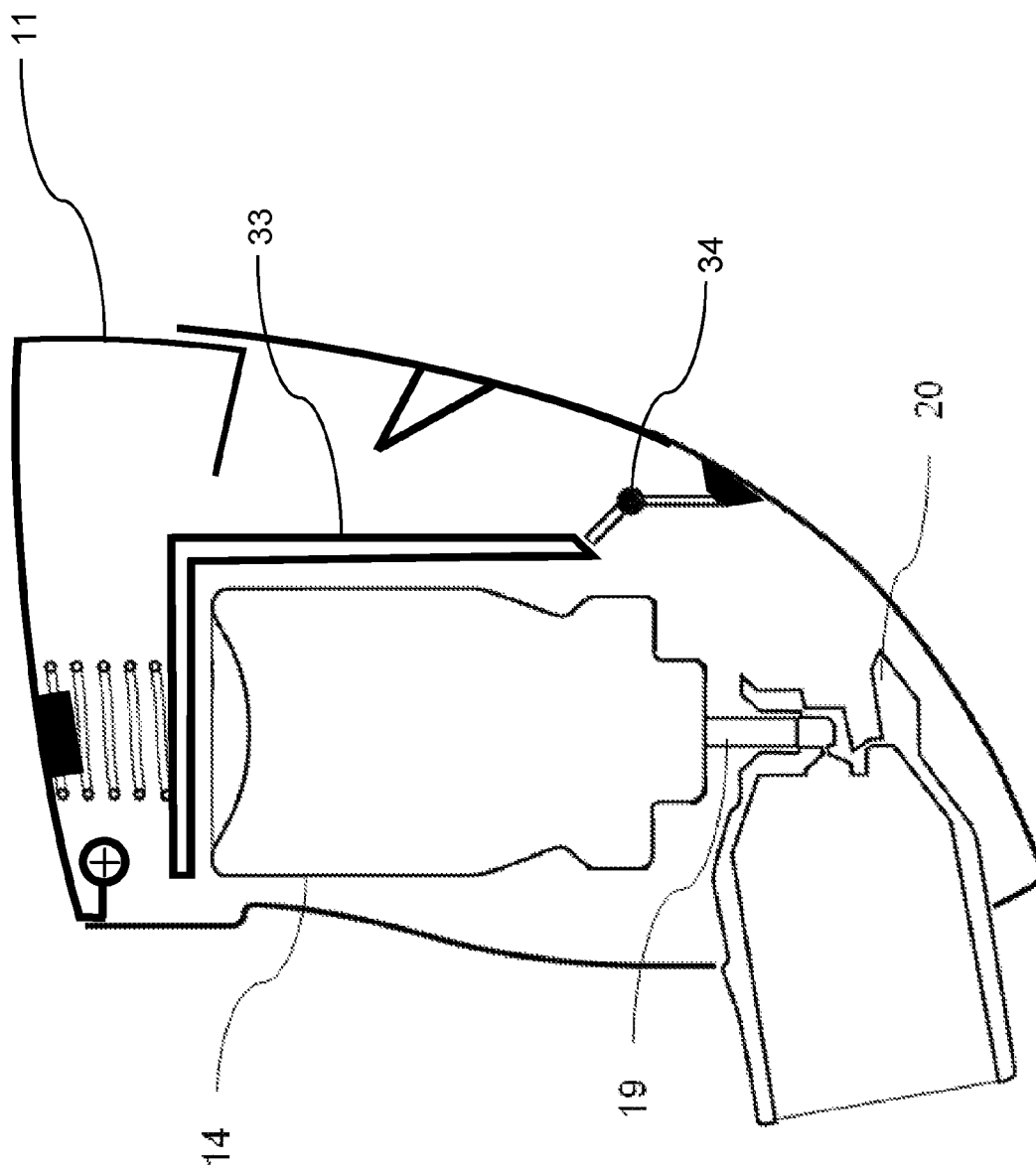
FIG. 15 illustrates another position of an element preventing compression.

FIG. 15 illustrates an alternative to the use of the element 18 in that this element is replaced by an element 33, which is positioned between the bottom of the canister 14 and the spring 13 and engages the spring 13. In this situation, depression of the button 11 and compression of the spring 13 will not provide force to the canister 14, which is still compressible by forcing the main part of the canister 14 downwards, due to the operation of the element 34.

The element 34 releases the element 33, when the flow in the flow channel 17 is sufficiently high, whereby operation generally is as that of the remaining figures, apart from the fact that the force of a depressed spring 13 only reaches the canister 14, when the flow is sufficient.

Naturally, all the above further features and embodiments may equally well be used in the embodiment of FIG. 15.

In general, it should be understood that the button 11 and the spring 13 may be replaced by numerous other types of elements—or may be dispensed with. The user may just as well simply engage the bottom of the canister 14.

Providing especially the spring 13 or another type of resilient element provides the advantage that the user may experience a movement while biasing the resilient element. This movement may facilitate the above indications to the person that the force applied is sufficient.

In addition, the flap element 15 may be replaced by any other means either directly displaceable/rotatable by the flow or simply by a flow sensor of any type connected to an element controllable to release or allow compression in any manner. Naturally, a processor or other controller may be used in that embodiment.

Figure 16:
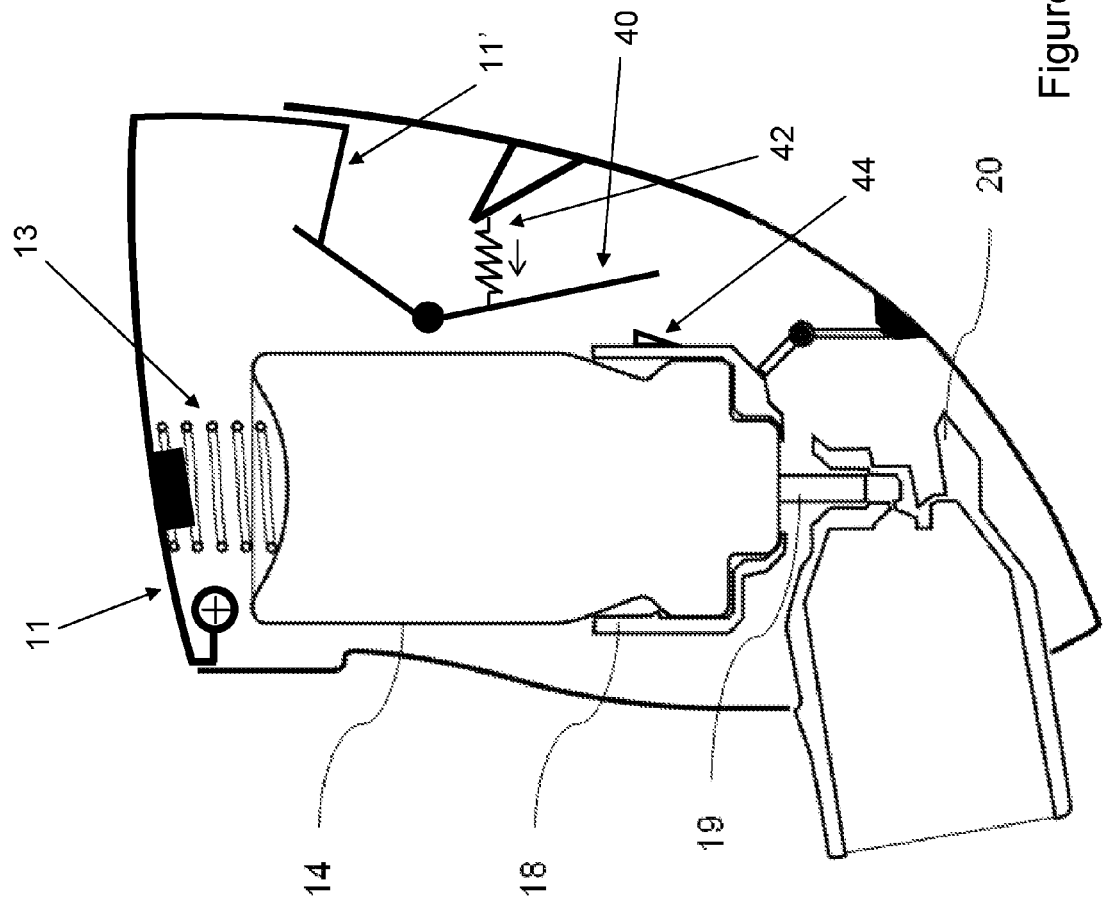
FIGS. 16-18 illustrate an embodiment comprising a locking element preventing the canister from reverting to its extended state.
Figure 17:
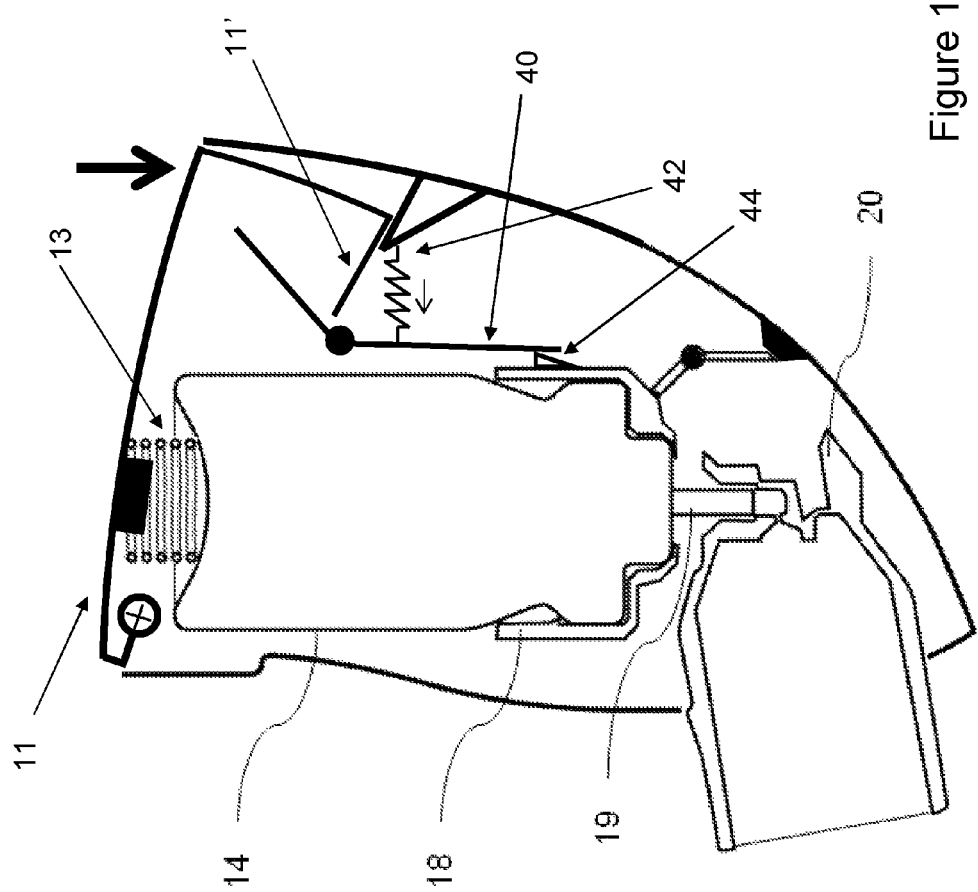
Figure 18:
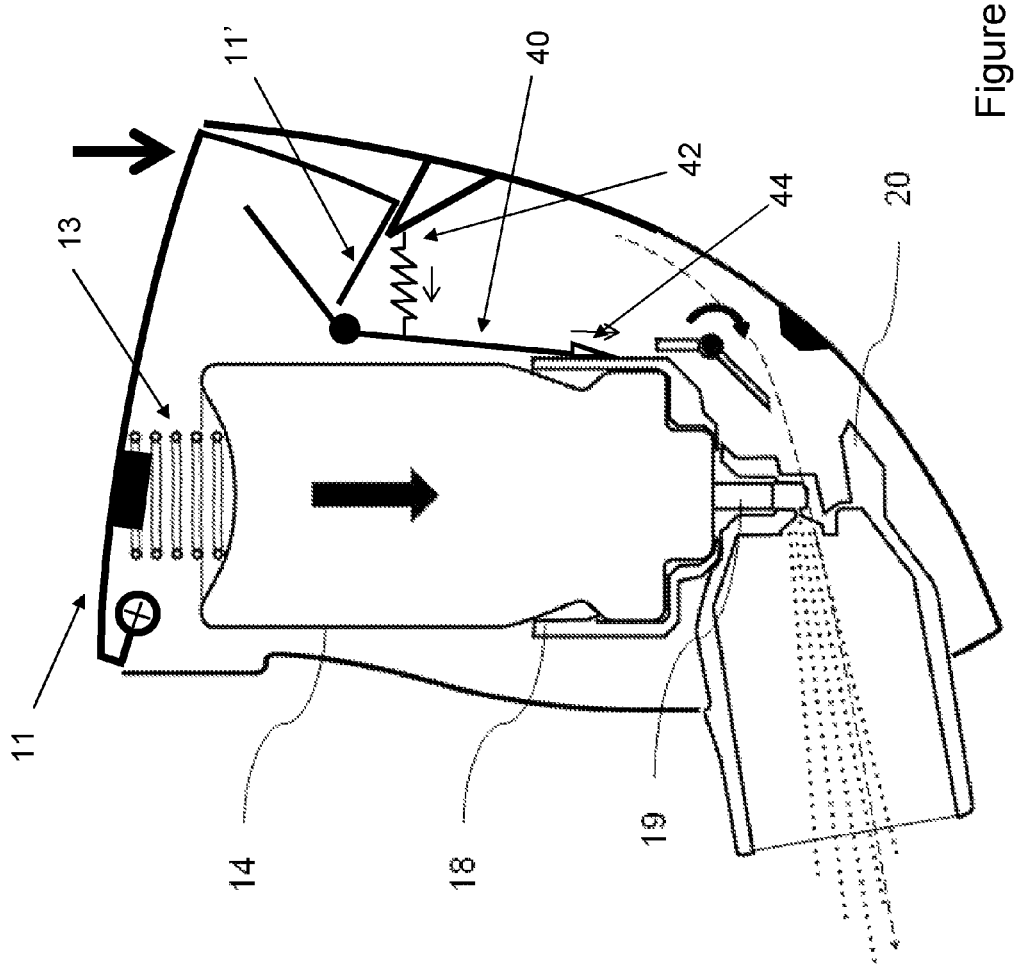

FIGS. 16-18 illustrate an embodiment wherein a blocking element 40 is provided which engages an inwardly extending part 11' of the button 11 and a projection 44 of the element 18. The blocking element 40 is biased, by a spring 42, toward a position at which it engages the projection 44 but may be forced away from that position by the operation of the extending part 11'.

The overall operation of the blocking element 40 is best illustrated when the button 11 has been depressed (see FIG. 17) in order to bias the canister 14 and allow dispensing of a dose of the medication. In this position, the extending portion 11' is at a sufficiently low position for the biasing spring 42 to operate and force the blocking element 40 toward the projection 44.

Once the canister 14 is allowed to compress (see FIG. 18), the blocking element 40 is allowed to engage the projection 44, now preventing the canister 14 from reverting to its extended state. The spring 42 will maintain this state, until the button 11 is released to a degree where the extending part 11' again engages the blocking element 40 and forces the blocking element 40 out of engagement with the projection 44.

This release of the projection 44 and element 18 takes place when the button 11 has been released to a degree where the force exerted by the spring 13 is lower than the force exerted by the canister 14 once allowed to extend. In this manner, it is ensured that the canister 14 is allowed to extend fully extend.

Thus, the interaction between the extending part 11' and the blocking element 40 is calibrated so that the blocking element 40 does not disengage the projection 44 until the button 11 is released to a degree where the force exerted by the spring 13 is lower than the force exerted by the canister 14 upon extending.

Figure 19:
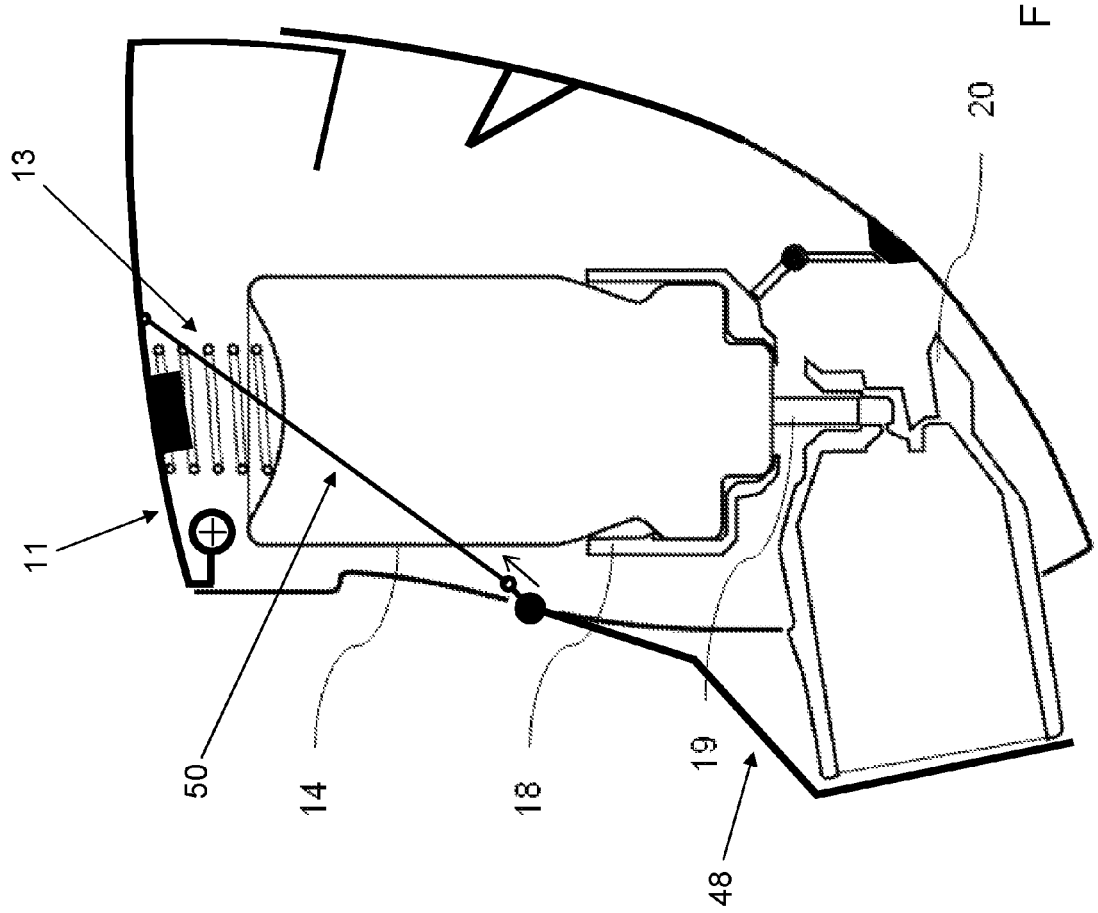
FIGS. 19-21 illustrate an embodiment comprising a lid.
Figure 20:
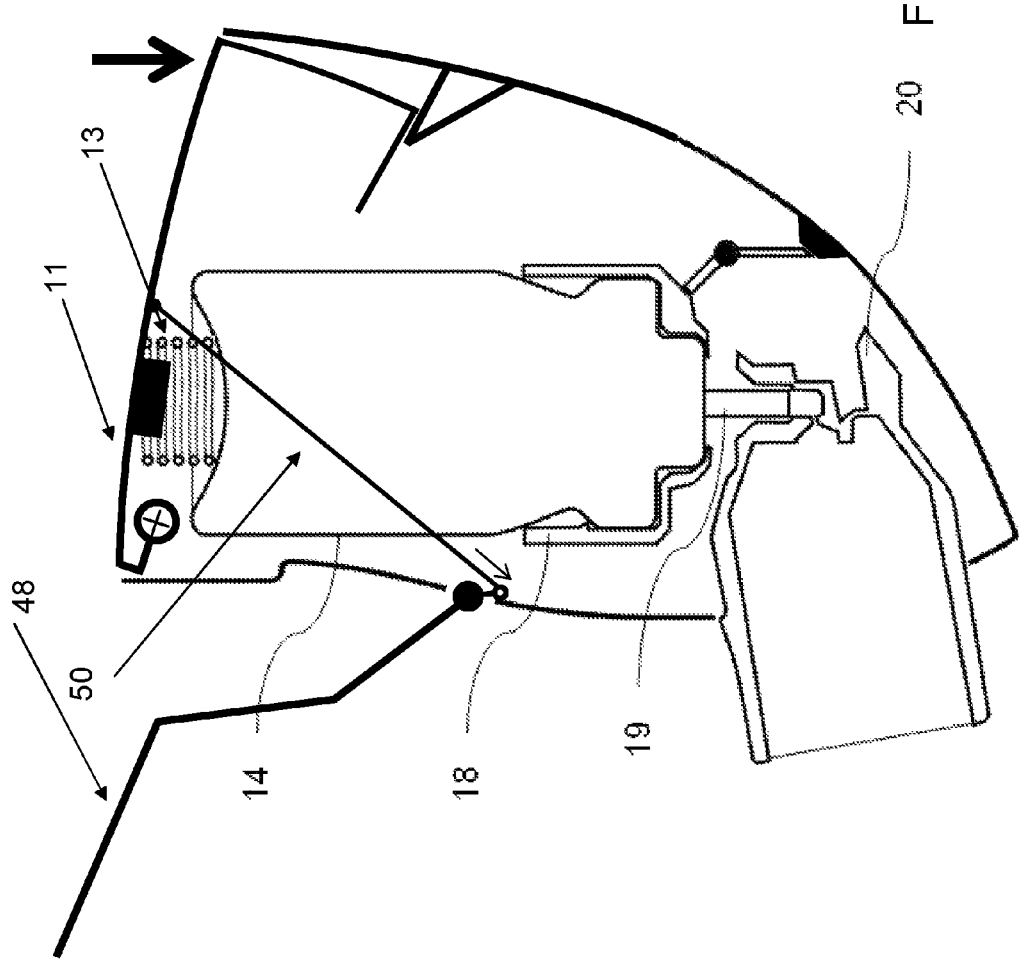
Figure 21:
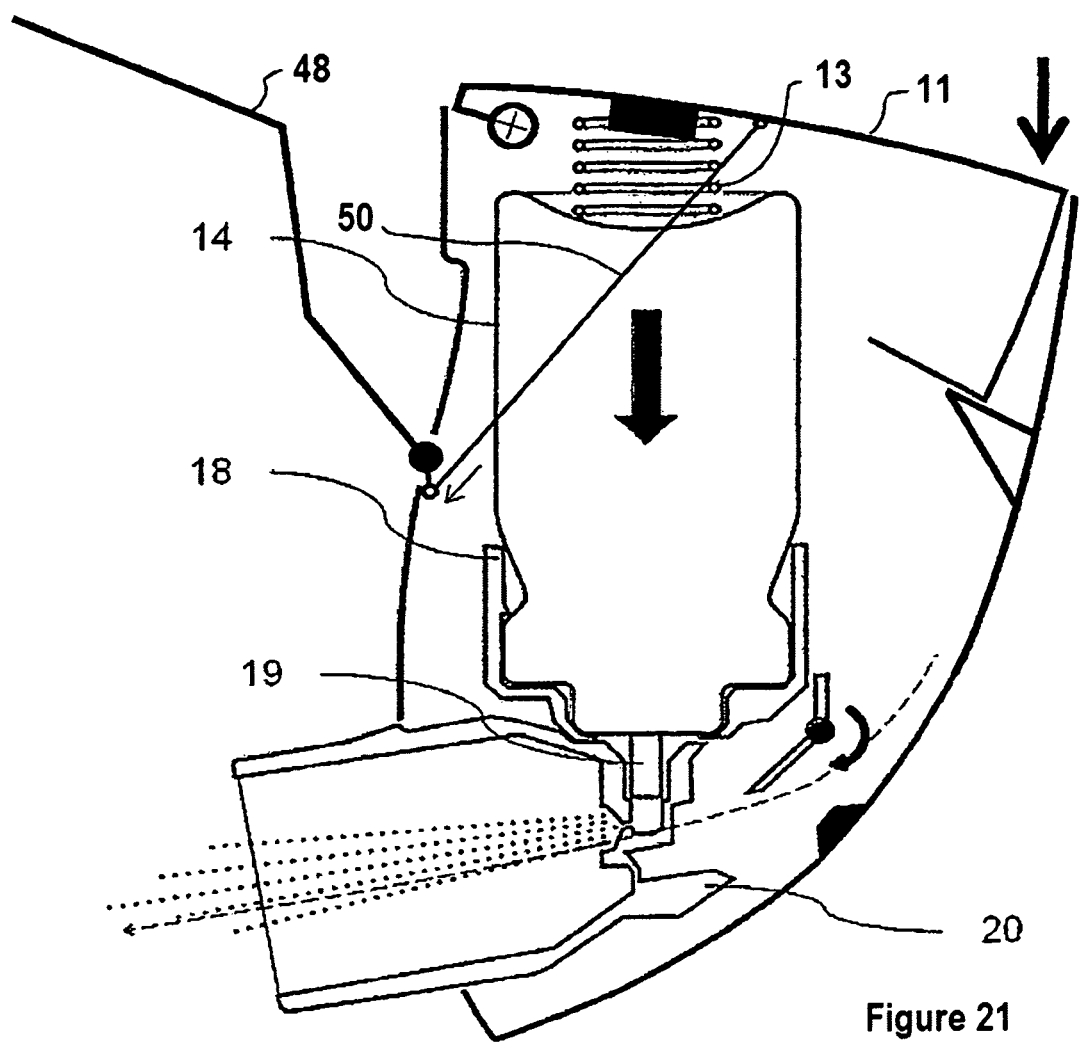

In FIGS. 19, 20 and 21, a final embodiment is illustrated in which a lid 48 (see FIG. 19) in a released position covers the opening of the mouth piece 20. Thus, it is ensured that the mouth piece 20 is not contaminated between uses.

When opening the lid 48 (see FIG. 20), the button 11 is depressed or forced downwards in order to bias the canister 14 and render the canister ready to administer a dose of the medication.

Preferably, the lid 48 is not able to stay in the position of FIG. 20 alone but must be maintained there by a user in order to obtain the advantage that the canister 14 is only biased as long as the user maintains the lid 48 in the open position.

Naturally, the button 11 need not be present in this embodiment. The lid 48 may affect the canister 14 in any other way, and the button 11 may be replaced by a closed top of the housing. Thus, the lid 48 or force exerting element 50 may affect the remote end of the spring 13 in any other way.

Furthermore, even though all illustrated embodiments relate to the engagement of the canister at the end pointing away from the stem 19, the engagement may equally well be at the stem, where the other end may be fixed in relation to the housing. This will give the same operation and advantages.

The invention claimed is:

1. A dispenser for providing aerosolized medication to a person in need thereof, the dispenser comprising:
   a canister outputting the medication upon compression of the canister along a first direction with a selected force, the medication being output into a flow channel,
   a first preventor preventing compression of the canister until a threshold minimum flow is present in the flow channel, a transferring element configured to receive a force from a user and to, at all times and in real time, transfer at least part of the force applied to the transferring element from the user to at least one of the canister and the first preventor along the first direction, and an indicator indicating to the user when the transferred force is equal to or exceeds the selected force, the dispenser having no lockable storage that stores energy or prevents a force that exceeds the selected force from being applied or removed.

2. The dispenser according to claim 1, wherein the indicator comprises an element being configured to at least substantially block the flow channel, when the transferred force is lower than the selected force.

3. The dispenser according to claim 1, wherein the canister comprises an output element, the canister being compressible by displacing the output element in a direction into the canister, wherein the transferring element is configured to transfer the force to the canister, and wherein the first preventor is configured to prevent displacement of the output element in the direction into the canister.

4. The dispenser according to claim 1, wherein the transferring element is configured to transfer the force to the first preventor.

5. The dispenser according to claim 1, wherein the transferring element is adapted to, when not engaged by the user, transfer at least substantially no force to the at least one of the canister and the first preventor.

6. The dispenser according to claim 1, further comprising a second preventor configured to prevent the canister from, upon compression, extending, until the transferred force is below the selected force.

7. The dispenser according to claim 1, wherein the transferring element comprises an element blocking, in a first position when the force received from the user is below the selected force, the flow channel and opening, in another position when the force received from the user exceeds the selected force, the flow channel.

8. The dispenser according to claim 1, wherein the dispenser has no lockable spring or latch.

9. The dispenser according to claim 1, wherein the force that exceeds the selected force from being applied or removed is a combination of at least the transferred force and a force due to inhalation.

10. The dispenser according to claim 1, wherein the transferring member is configured to receive a manual force from the user.

11. A method of operating the dispenser according to claim 1, the method comprising the steps of:

the user providing the force to the transferring element which transfers to the at least one of the canister and the first preventor the force exceeding the selected force, while any gas flow in the flow channel is lower than the threshold minimum flow, the indicator simultaneously indicating to the user that the transferred force is equal to or exceeds the selected force, the user subsequently releasing the transferring element, whereby at least substantially no force is subsequently transferred to the at least one of the canister and the first preventor.

* * * * *